United States Patent
Zhu et al.

(10) Patent No.: US 11,559,477 B2
(45) Date of Patent: Jan. 24, 2023

(54) PREPARATION METHOD AND USE OF ARTIFICIAL EXOSOME COMPLEX

(71) Applicant: SHANGHAI CHEERMORE BIOLOGICAL TECHNOLOGY CO., LTD., Shanghai (CN)

(72) Inventors: Caibin Zhu, Shanghai (CN); Junxiang Li, Shanghai (CN)

(73) Assignee: SHANGHAI CHEERMORE BIOLOGICAL TECHNOLOGY CO., LTD., Shanghai (CN)

( * ) Notice: Subject to any disclaimer, the term of this patent is extended or adjusted under 35 U.S.C. 154(b) by 0 days.

(21) Appl. No.: 17/436,656

(22) PCT Filed: Apr. 27, 2020

(86) PCT No.: PCT/CN2020/087344
§ 371 (c)(1),
(2) Date: Sep. 7, 2021

(87) PCT Pub. No.: WO2020/182226
PCT Pub. Date: Sep. 17, 2020

(65) Prior Publication Data
US 2022/0096354 A1 Mar. 31, 2022

(30) Foreign Application Priority Data
Mar. 12, 2019 (CN) .......................... 201910183081.6

(51) Int. Cl.
*A61K 47/36* (2006.01)
*A61K 47/18* (2017.01)
*A61K 8/41* (2006.01)
*A61K 8/60* (2006.01)
*A61K 8/73* (2006.01)
*A61Q 19/00* (2006.01)
*A61K 8/84* (2006.01)

(52) U.S. Cl.
CPC ................ *A61K 8/735* (2013.01); *A61K 8/84* (2013.01); *A61Q 19/00* (2013.01); *A61K 2800/5922* (2013.01)

(58) Field of Classification Search
None
See application file for complete search history.

(56) References Cited

U.S. PATENT DOCUMENTS

2012/0202283 A1* 8/2012 Koyama ............... A61K 47/542
435/320.1

FOREIGN PATENT DOCUMENTS

| CN | 101270168 A | 9/2008 |
| CN | 101821317 A | 9/2010 |
| CN | 102408498 A | 4/2012 |
| CN | 103665384 A | 3/2014 |
| CN | 110638690 A | 1/2020 |

OTHER PUBLICATIONS

Lutz Tauhardt, et al. Linear Polyethyleneimine: Optimized Synthesis and Characterization—On the Way to "Pharmagrade" Batches, Macromol. Chem. Phys., 2011, pp. 1918-1924, vol. 212, No. 17.
Kitae Park, et al., Reducible Hyaluronic Acid-siRNA Conjugate for Target Specific Gene Silencing, Bioconjugate Chemistry, 2013, pp. 1201-1209, vol. 24, No. 7.
Kitae Park, et al. Target Specific Systemic Delivery of TGF-B siRNA/(PEI-SS)-g-HA complex for the treatment of liver cirrhosis, Biomaterials, 2011, pp. 4951-4958, vol. 32.
Saibom Park, et al. Dual Roles of Hyaluronic Acids in Multilayer Films Capturing Nanocarriers for Drug-Eluting Coatings, Biomaterials, 2012, pp. 5468-5477, vol. 33.

* cited by examiner

*Primary Examiner* — Brian Gulledge
(74) *Attorney, Agent, or Firm* — Bayramoglu Law Offices LLC

(57) ABSTRACT

A preparation method and use of an artificial exosome complex are provided. Raw materials for preparing the artificial exosome complex include linear polyethyleneimine (PEI) and hyaluronic acid (HA). The linear PEI can be obtained through the HA-PEI preparation process of the present disclosure, and most PEI is branched currently. According to the HA-PEI preparation method, HA-PEI with a specific molecular weight can be quantitatively prepared. The preparation process involves controllable operation steps, and thus can be used for large-scale industrial production. The prepared HA-PEI can promote the absorption of an encapsulated active substance by deep skin cells through the ligand activity of HA and the membrane permeability of linear PEI.

4 Claims, 2 Drawing Sheets

PREPARATION METHOD AND USE OF ARTIFICIAL EXOSOME COMPLEX

CROSS REFERENCE TO THE RELATED APPLICATIONS

This application is the national phase entry of International Application No. PCT/CN2020/087344, filed on Apr. 27, 2020, which is based upon and claims priority to Chinese Patent Application No. 201910183081.6, filed on Mar. 12, 2019, the entire contents of which are incorporated herein by reference.

TECHNICAL FIELD

The present disclosure belongs to the technical field of biochemistry, and specifically relates to a preparation method and the use of an artificial exosome complex.

BACKGROUND

The effectiveness of a skin care product mainly depends on the absorption efficiency of an active substance, but there are few effective media for delivering active substances on the present market. Linear polyethyleneimine (PEI) has both hydrophilic and lipophilic groups, such that the linear PEI can form a bilayer with the hydrophilic groups inside and the lipophilic groups outside, and can encapsulate a substance to form a microcapsule. The microcapsule can fuse with a cell membrane due to its own membrane fusion property and then deliver an inclusion into a cell. However, due to the utilization of the membrane fusion property, the microcapsule has no cell selectivity. Hyaluronic acid (HA), also known as hyaluronan, is a natural moisturizing lubricant having a large molecular weight, and HA cannot be effectively absorbed by deep skin cells, which exhibits limited skin care persistence.

There is no combination of linear PEI and HA on the present market. A technical difficulty for the combination of linear PEI and HA is that linear PEI and HA are not simply mixed together, but are truly linked together through an amidation reaction to form a microcapsule similar to an exosome. Linear PEI and HA are both high polymers, rather than small-molecule compounds, so there is an extremely high technical difficulty in the control of such a reaction and a product quality.

SUMMARY

At least one technical problem solved by the present disclosure is to provide a preparation method and the use of a new artificial exosome complex. The present disclosure is intended to fuse linear PEI and HA, such that HA and PEI can play a synergistic role in a skin care product through the ligand activity of HA and the membrane permeability of PEI to facilitate the effective absorption of an active substance into deep skin cells.

In order to achieve the above objective, the present disclosure adopts the following technical solutions: An artificial exosome complex is provided, where raw materials for preparing the artificial exosome complex include linear PEI and HA.

Further, the HA may be composed of disaccharide units that each are formed by D-glucuronic acid and N-acetylglucosamine, and the HA may have a molecular weight of 400 to 1,800,000 and the HA may exist in the form of HA or sodium hyaluronate (SH).

Further, the linear PEI may be obtained by heating and hydrolyzing poly(2-ethyl-2-oxazoline) in a sulfuric acid aqueous solution, and may have a molecular weight of 1,000 to 100,000.

Further, the artificial exosome complex may further include an amido bond, or include ethyl, imino, tertiary amino, amido, etc.

Further, the artificial exosome complex may be prepared into an aqueous solution with a concentration of 1 mg/mL to 1 g/mL.

A preparation method of the artificial exosome complex is also provided, including the following steps:

a. dissolving 45 g of poly(2-ethyl-2-oxazoline) in 200 mL of a 30% sulfuric acid aqueous solution to obtain a reaction solution, and setting up a heating reflux device;

b. heating the reaction solution to allow a reaction at reflux, and continuously detecting a pH of a distilled solution to determine propionic acid (a reaction by-product) until there is no propionic acid in the distilled solution; and when the pH of the distilled solution is 6.0 to 7.0, stopping the reaction; wherein the propionic acid can form an azeotrope with water, and the reaction takes about 7 d;

c. after the reaction was stopped, cooling a resulting reaction system to 0° C., and starting clockwise one-way mechanical stirring at a speed of 300 rpm; and adjusting a pH of the reaction system to 7.0 by adding a sodium hydroxide solution with a concentration of 1 mol/L dropwise, and adjusting the pH to 10 to 11 by adding a small amount of the sodium hydroxide solution dropwise;

d. during the process of adjusting the pH, precipitating out a solid slowly, wherein the solid is PEI;

e. after the solid is completely precipitated out, filtering out the solid, and washing the solid with a large amount of distilled water until a resulting filtrate changes to neutral from alkaline;

f. vacuum-drying the solid at room temperature until there is no residual moisture, wherein the vacuum-drying takes about 7 d;

g. adding 600 mg of HA and 300 mL of distilled water to a beaker 1 to prepare a solution A; adding 12 g of the PEI and 300 ml of distilled water to a beaker 2 to prepare a solution B; adding the solution A to the solution B, and adjusting a pH of a resulting mixed solution to 6.5 with a 1 M HCl solution to obtain a solution C; dissolving 6.3 mmol of 1-ethyl-3-(3-dimethylaminopropyl)carbodiimide (EDC, water-soluble carbodiimide) and 6.3 mmol of 1-hydroxybenzotriazole (HOBt) in a mixed solvent formed by 15 mL of distilled water and 15 mL of dimethyl sulfoxide (DMSO) to obtain a solution D; and adding the solution C and the solution D to a 1.5 L round-bottom flask, stirring a resulting mixed solution at room temperature for 24 h, and adjusting a pH of the resulting mixed solution to 7.0 with a 1 M NaOH solution to obtain a reaction solution;

h. adding the reaction solution to an activated dialysis bag (8,000 KD to 14,000 KD), and dialyzing in a 100 mM NaCl solution for 2 d, then in ethanol with a volume fraction of 25% for 1 d, and finally in pure water for 1 d to obtain an HA-PEI liquid; and lyophilizing the HA-PEI liquid for 2 d to obtain a white spongy HA-PEI substance;

i. dispersing 10 g of the lyophilized HA-PEI into 50 mL of distilled water, adjusting a pH to 7.1 with a dilute hydrochloric acid solution, and adding distilled water to 100 mL; and j. using a 0.2 μm filter membrane to sterilize a resulting solution to obtain an HA-PEI stock solution with a concentration of 100 mg/mL.

The use of the artificial exosome complex is also provided, where the artificial exosome complex is prepared into a preparation capable of significantly promoting the absorption of an active substance in a deep skin layer through an HA receptor.

Further, the preparation may be in any clinically-acceptable dosage form.

Further, the artificial exosome complex may be used as the sole active ingredient to prepare the preparation capable of promoting the absorption of an active substance by skin, or is used in combination with other substances to prepare the preparation capable of promoting the absorption of an active substance by skin.

Compared with the prior art, the present disclosure has the following advantages:

1) According to the HA-PEI preparation process of the present disclosure, linear PEI can be obtained. Because most PEI is branched currently and branched PEI has few imino groups, it is difficult to form a microcapsule structure. Therefore, linear PEI is one of the key advantages to form the artificial exosome.

2) With the HA-PEI preparation method of the present disclosure, HA-PEI with a specific molecular weight can be quantitatively prepared. Because a molecular weight of HA-PEI depends on molecular weights of HA and PEI and the molecular weight of PEI depends on a molecular weight of poly(2-ethyl-2-oxazoline), HA-PEI with a specific molecular weight can be quantitatively prepared, that is, a size of the artificial exosome can be quantitatively controlled.

3) The operation steps of the present disclosure are controllable, which is suitable for large-scale industrial production. Because the preparation process of the present disclosure is safe and environmentally-friendly and has no amplification effect, the conditions for industrial production are met.

4) The HA-PEI of the present disclosure can promote the absorption of an encapsulated active substance by deep skin cells through the ligand activity of HA and the membrane permeability of linear PEI.

DETAILED DESCRIPTION OF THE EMBODIMENTS

The present disclosure is further explained below in conjunction with specific examples, but the present disclosure is not limited thereto.

In the following examples, unless otherwise specified, the methods used are conventional methods, and all reagents used are commercially-available products.

Example 1. Detection of Skin Irritation of the Artificial Exosome Complex

The detection method is as follows.

10 volunteers were recruited; a freshly-prepared artificial exosome solution with a concentration of 1 mg/mL was evenly applied at an inner side of the left wrist, and double distilled water (DDW) was applied at an inner side of the right wrist, which used as a control group; and after the application, the changes of the inner side of the wrist that was standing was continuously observed for 20 min and it was recorded whether the volunteer had pain, itch, and other irritating symptoms.

Figure 1:
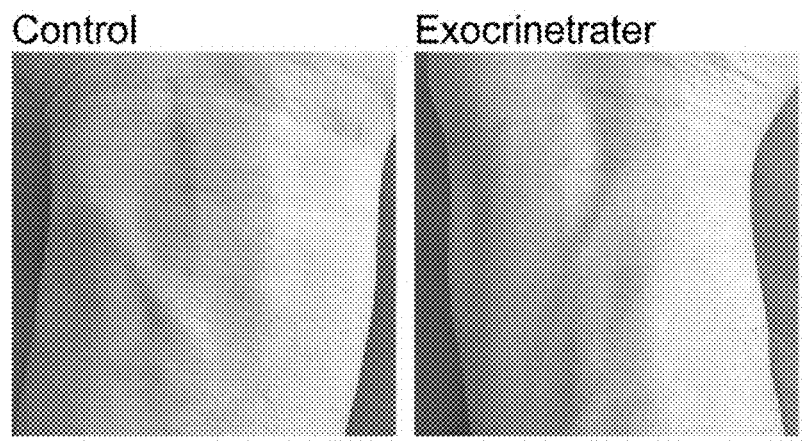
FIG. 1 shows the skin irritation detection result for the artificial exosome according to one aspect of the present disclosure (Control: control group; and Exocrinetrater: artificial exosome group)

Experimental results were shown in FIG. 1.

TABLE 1

Statistical results of the skin test for the artificial exosome

| | | Control (number of volunteers) | Exocrinetrater (number of volunteers) |
|---|---|---|---|
| Pain | Yes | 0 | 0 |
| | No | 10 | 10 |
| Itch | Yes | 0 | 0 |
| | No | 10 | 10 |
| Redness and Swelling | Yes | 0 | 0 |
| | No | 10 | 10 |

The experimental conclusion is as follows.

Within the 20 min after the artificial exosome was applied, none of the 10 volunteers experienced the skin irritation symptom of redness and swelling, and none of the 10 volunteers had irritating pain, itch, etc.

Example 2. Detection of Cytotoxicity of the Artificial Exosome

The detection method is as follows.

Human immortal keratinocyte cells (HaCaT cells) were cultivated, digested, and inoculated in a 96-well plate at 5,000 cells/well; the artificial exosome was prepared into artificial exosome solutions with gradient concentrations, the solutions were added to the HaCaT cells, separately, and the cells were further cultivated for 48 h, the morphology of the cells was observed during the 48 h; and finally the MTT method was used to detect the influence of the artificial exosome on cell proliferation.

Figure 2:
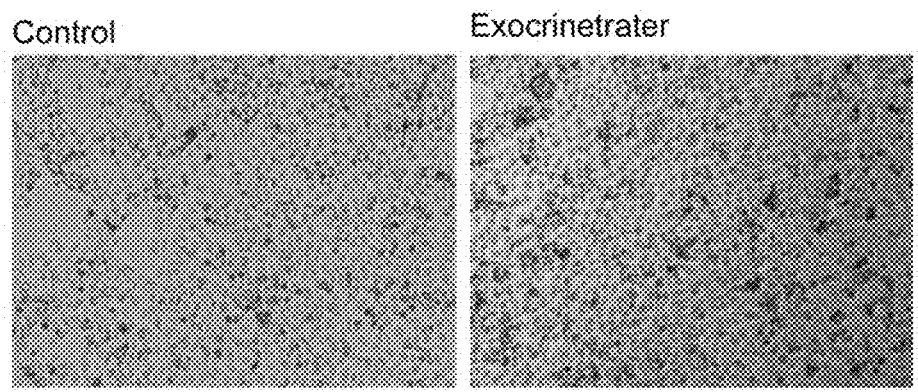
FIG. 2 shows the influence of the artificial exosome on the morphology of HaCat cells according to one aspect of the present disclosure (Control: control group; and Exocrinetrater: artificial exosome group)
Figure 3:
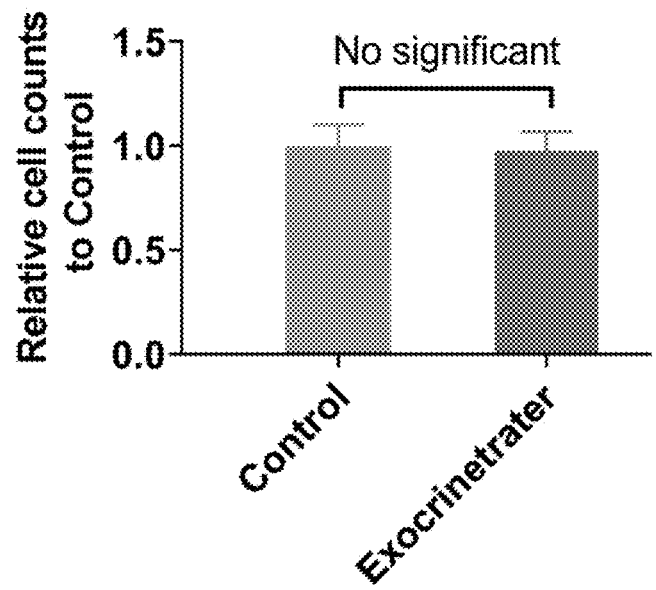
FIG. 3 shows the influence of the artificial exosome on the proliferation of HaCat cells according to one aspect of the present disclosure (Control: control group; and Exocrinetrater: artificial exosome group)

Experimental results were shown in FIG. 2 and FIG. 3.

The experimental conclusion is as follows.

The artificial exosome did not show obvious cytotoxicity at the cell level, and had no influence on the cell proliferation.

Example 3. Detection of the Delivery Efficiency of the Artificial Exosome for an Active Substance The detection method is as follows.

The activity of the green fluorescent protein (GFP)-encoding plasmid pCDNA3.1-eGFP that was delivered by the artificial exosome into HaCat cells was detected.

Figure 4:
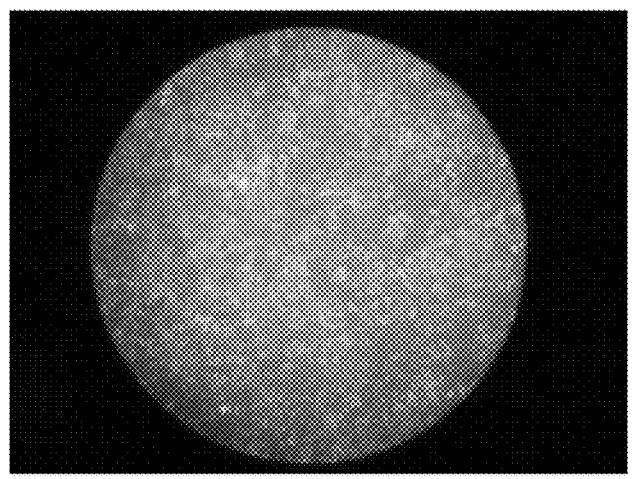
FIG. 4 shows the detection result of the delivery efficiency of the artificial exosome for pCDNA3.1-eGFP according to one aspect of the present disclosure.

Experimental results were shown in FIG. 4.

The experimental conclusion is as follows.

The artificial exosome can well encapsulate an active substance and effectively deliver the active substance into cells.

Example 4. Detection of the Delivery Route of the Artificial Exosome for an Active Substance The detection method is as follows.

In order to further detect the delivery route of the artificial exosome for an active substance, intracellular organelles such as mitochondrion and lysosome were stained, and at the same time, the artificial exosome was used to deliver the GFP-encoding plasmid pCDNA3.1-eGFP. The delivery area of the active substance was analyzed through the positioning information of fluorescence.

Figure 5:
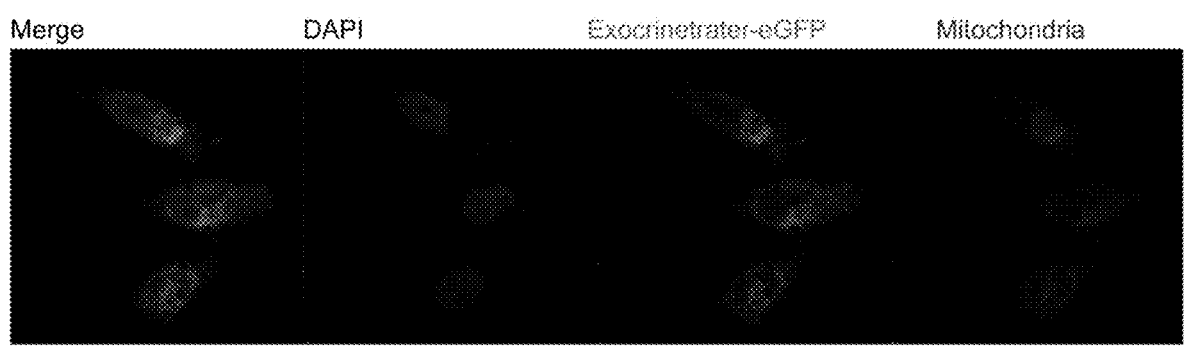
FIG. 5 shows the detection result of the delivery route of the artificial exosome according to one aspect of the present disclosure (DAPI: nuclear stain; Exocrinetrater: artificial exosome; and Mitochondria: mitochondrion)

Experimental results were shown in FIG. 5.

The experimental conclusion is as follows.

It shows that the artificial exosome can directly deliver the active substance to mitochondria, and it is speculated that, through this delivery route, the active substance can regulate the mitochondrial function, promote the stability of the mitochondrial function, and finally achieve the effect of anti-inflammation and cytothesis.

Example 5. Detection of the Influence of the Artificial Exosome on the Activity of Rat Skin The detection method is as follows.

Vista rats were used as experimental animals, and sodium carboxymethyl cellulose (CMC-Na) was used to prepare an artificial exosome encapsulating an active substance into an artificial exosome solution with a concentration of 1 mg/mL. The artificial exosome solution was continuously applied on the back of the rats for one week, and the control group was applied with a CMC-Na gel in which the active substance was dissolved. One week later, skin tissue was collected from the back of rats, immunofluorescence assay (IFA) was conducted to detect the expression of the active protein Cytokeratin for epidermal cells, and the functional penetration of the artificial exosome was reflected through the intensity of fluorescence.

Figure 6:
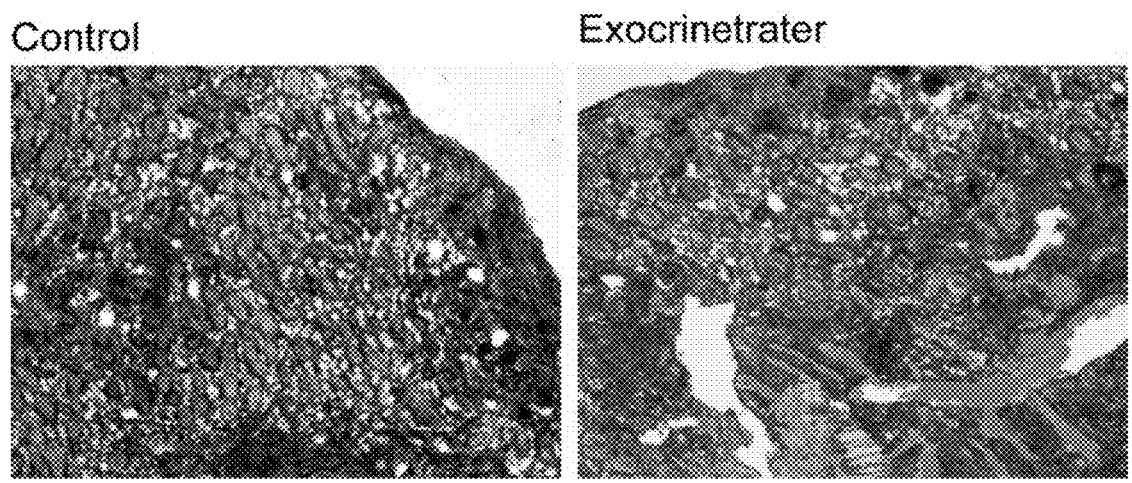
FIG. 6 shows the influence of the artificial exosome on the activity of rat skin according to one aspect of the present disclosure (Control: control group; and Exocrinetrater: artificial exosome group).

Experimental results were shown in FIG. 6.

The experimental conclusion is as follows.

Epithelial cells, when in an active state, express the membrane protein. In the IFA, the expression of Cytokeratin can be reflected through the intensity of green fluorescence, thereby reflecting the activity of epidermal cells. It can be seen from the results that the active substance without the artificial exosome cannot effectively stimulate the expression of Cytokeratin, that is, the cell activity cannot be effectively activated; in contrast, the active substance in the artificial exosome stimulates the high expression of Cytokeratin on the skin tissue cells, that is, the artificial exosome activates the activity of epidermal cells and is conducive to the absorption of an active substance by cells. Moreover, the experimental results show that the artificial exosome can effectively activate the activity of deep skin cells. Since the artificial exosome includes HA, it is speculated that cells in the superficial skin layer such as the cuticular layer and stratum lucidum cannot effectively adsorb the artificial exosome as it cannot effectively express an HA receptor, such that the active substance can be delivered deeply to the prickle cell layer and basal cell layer with HA receptors, which makes the skin care more effective.

Although the examples of the present disclosure have been illustrated and described, it should be understood that those of ordinary skill in the art may make various changes, modifications, replacements and variations to the above examples without departing from the principle and spirit of the present disclosure, and the scope of the present disclosure is limited by the appended claims and legal equivalents thereof.

What is claimed is:

1. A preparation method of an artificial exosome complex, wherein raw materials for preparing the artificial exosome complex comprise linear polyethyleneimine (PEI) and hyaluronic acid (HA), and the preparation method comprises the following steps:
   a. dissolving 45 g of poly(2-ethyl-2-oxazoline) in 200 mL of a 30% sulfuric acid aqueous solution to obtain a reaction solution, and setting up a heating reflux device;
   b. heating the reaction solution to allow a reaction at reflux, and continuously detecting a pH of a distilled solution to determine propionic acid (a reaction by-product) until there is no propionic acid in the distilled solution; and stopping the reaction when the pH of the distilled solution is 6.0 to 7.0; wherein the propionic acid forms an azeotrope with water, and the reaction takes about 7 d;
   c. after the reaction was stopped, cooling a resulting reaction system to 0° C., and starting clockwise one-way mechanical stirring at a speed of 300 rpm; and adjusting a pH of the reaction system to 7.0 by adding a sodium hydroxide solution with a concentration of 1 mol/L dropwise, and adjusting the pH to 10 to 11 by adding a small amount of the sodium hydroxide solution;
   d. during the process of adjusting the pH, precipitating out a solid slowly;
   e. filtering out the solid, and washing the solid with a large amount of distilled water until a resulting filtrate changes to neutral from alkaline;
   f. vacuum-drying the solid at room temperature until there is no residual moisture, wherein the vacuum-drying takes about 7 d;
   g. adding 600 mg of HA and 300 mL of distilled water to a first beaker to prepare a first solution; adding 12 g of the PEI and 300 ml of distilled water to a second beaker to prepare a second solution; adding the first solution to the second solution, and adjusting a pH of a resulting mixed solution to 6.5 with a 1 M HCl solution to obtain a third solution; dissolving 6.3 mmol of 1-ethyl-3-(3-dimethylaminopropyl)carbodiimide (EDC) and 6.3 mmol of 1-hydroxybenzotriazole (HOBt) in a mixed solvent formed by 15 mL of distilled water and 15 mL of dimethyl sulfoxide (DMSO) to obtain a fourth solution to a 1.5 L round bottom flask; and adding the third solution and the fourth solution, stirring a resulting mixed solution at room temperature for 24 h, and adjusting a pH of the resulting mixed solution to 7.0 with a 1M NaOH solution to obtain a reaction solution;
   h. adding the reaction solution to an activated dialysis bag of 8,000 KD to 14,000 KD, and dialyzing in a 100 mM NaCl solution for 2 d, then in ethanol with a volume fraction of 25% for 1 d, and finally in pure water for 1 d to obtain an HA-PEI liquid; and lyophilizing the HA-PEI liquid for 2 d to obtain a white spongy HA-PEI substance;
- i. dispersing 10 g of the lyophilized HA-PEI into 50 mL of distilled water, adjusting a pH to 7.1 with a dilute hydrochloric acid solution, and adding distilled water to 100 mL; and
- j. using a 0.2 μm filter membrane to sterilize a resulting solution to obtain an HA-PEI stock solution with a concentration of 100 mg/mL to produce the artificial exosome complex.

2. The preparation method according to claim 1, wherein the artificial exosome complex is prepared into an aqueous solution with a concentration of 1 mg/mL to 1 g/mL.

3. The preparation method according to claim 1, wherein the HA is disaccharide units composed of D-glucuronic acid and N-acetylglucosamine, and the HA has a molecular weight of 400 to 1,800,000 and is in the form of the HA and sodium hyaluronate (SH).

4. The preparation method according to claim 1, wherein the linear PEI is obtained by heating and hydrolyzing the poly(2-ethyl-2-oxazoline) in a sulfuric acid aqueous solution, and has a molecular weight of 1,000 to 100,000.

\* \* \* \* \*